United States Patent
Pastore et al.

(10) Patent No.: US 6,752,839 B1
(45) Date of Patent: *Jun. 22, 2004

(54) COMPOSITION FOR OXIDATION DYEING OF KERATIN FIBRES AND DYEING PROCESSES USING THESE COMPOSITIONS

(75) Inventors: Florent Pastore, Rueil Malmaison (FR); Alain Lagrange, Coupvray (FR)

(73) Assignee: L'Oreal, Paris (FR)

( * ) Notice: Subject to any disclaimer, the term of this patent is extended or adjusted under 35 U.S.C. 154(b) by 142 days.

This patent is subject to a terminal disclaimer.

(21) Appl. No.: 09/692,715

(22) Filed: Oct. 20, 2000

(30) Foreign Application Priority Data

Oct. 21, 1999 (FR) .......................................... 99 13148

(51) Int. Cl.$^7$ ................................................ A61K 7/13
(52) U.S. Cl. ...................... 8/405; 8/406; 8/407; 8/408; 8/409; 8/411; 8/412
(58) Field of Search .......................... 8/407, 408, 409, 8/411, 412, 405, 406

(56) References Cited

U.S. PATENT DOCUMENTS

| | | | | |
|---|---|---|---|---|
| 4,003,699 | A | 1/1977 | Rose et al. | 8/10.2 |
| 4,823,985 | A | 4/1989 | Grollier et al. | 221/1 |
| 5,061,289 | A | 10/1991 | Clausen et al. | |
| 5,334,225 | A | 8/1994 | Ogawa et al. | 8/408 |
| 5,380,340 | A | 1/1995 | Neunhoeffer et al. | 8/409 |
| 5,538,517 | A | * 7/1996 | Samain et al. | 8/423 |
| 5,766,576 | A | 6/1998 | Löwe et al. | 424/62 |
| 5,769,903 | A | * 6/1998 | Audousset et al. | 8/409 |
| 6,099,593 | A | 8/2000 | Terranova et al. | 8/409 |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 0 579 204 | 1/1994 |
| DE | 195 43 988 | 5/1997 |
| DE | 196 04 178 | 8/1997 |
| FR | 2 586 913 | 3/1987 |
| FR | 2 733 749 | 11/1996 |
| FR | 2 750 048 | 12/1997 |
| JP | 219576 | 1/1990 |
| JP | 2521636 | 5/1996 |
| JP | 9-110659 | 4/1997 |
| WO | WO 94/08969 | 4/1994 |
| WO | WO 94/08970 | 4/1994 |
| WO | WO 96/15765 | 5/1996 |
| WO | WO-9719998 | * 6/1997 |

OTHER PUBLICATIONS

Co–pending Application No. 09/692,589; Attorney Docket No. 05725.0786–00000 Title: Composition For Oxidation Dyeing of Keratin Fibres and Dyeing Processes Using These Compositions Inventor(s): Florent Pastore et al. U.S. Filing Date: Oct. 20, 2000.

Co–pending Application No. 09/692,355; Attorney Docket No. 05725.0787–00000 Title: Composition For Oxidation Dyeing of Keratin Fibres and Dyeing Processes Using These Compositions Inventor(s): Florent Pastore et al. U.S. Filing Date: Oct. 20, 2000.

Co–pending Application No. 09/692,356; Attorney Docket No. 05725.0788–00000 Title: Composition For Oxidation Dyeing of Keratin Fibres and Dyeing Processes Using These Compositions Inventor(s): Florent Pastore et al. U.S. Filing Date: Oct. 20, 2000.

Co–pending Application No. 09/692,146; Attorney Docket No. 05725.0789–00000 Title: Composition For Oxidation Dyeing of Keratin Fibres and Dyeing Processes Using These Compositions Inventor(s): Florent Pastore et al. U.S. Filing Date: Oct. 20, 2000.

English language Derwent Abstract of DE 196 04 178. Aug. 7, 1997.

English language Derwent Abstract of FR 2 733 749. Nov. 8, 1996.

English language Derwent Abstract of JP 2–19576. Jan. 1990.

English language Derwent Abstract of JP 9–110659. Apr. 1997.

* cited by examiner

Primary Examiner—Yogendra N. Gupta
Assistant Examiner—Eisa Elhilo
(74) Attorney, Agent, or Firm—Finnegan Henderson Farabow Garrett & Dunner, L.L.P.

(57) ABSTRACT

Compositions for oxidation dyeing of keratin fibers, and in particular of human keratin fibers such as the hair, comprising, in a medium which is suitable for dyeing, at least one heterocyclic oxidation base chosen from pyrazoles, certain pyrimidines, pyrazolopyrimidines and the acid addition salts thereof, and at least one coupler chosen from 2-substituted 5-aminoalkylphenol derivatives and the acid addition salts thereof, as well as dyeing processes using these compositions.

65 Claims, No Drawings

COMPOSITION FOR OXIDATION DYEING OF KERATIN FIBRES AND DYEING PROCESSES USING THESE COMPOSITIONS

The present invention is directed to compositions for oxidation dyeing of keratin fibres comprising: at least one heterocyclic oxidation base chosen from pyrazoles, certain pyrimidines, pyrazolopyrimidines and the acid addition salts thereof and at least one coupler chosen from 2-substituted 5-aminoalkylphenol derivatives and the acid addition salts thereof, in a medium which is suitable for dyeing. The inventive compositions can be used for oxidation dyeing of human keratin fibres such as hair. The present invention is also directed to dyeing processes using these compositions.

Dye compositions comprising oxidation dye precursors are known in the art for dyeing keratinous fibres, in particular human hair. These oxidation dye precursors include ortho-phenylenediamines, para-phenylenediamines, ortho-aminophenols, para-aminophenols and heterocyclic bases. These are generally known as oxidation bases. The oxidation dye precursors, or oxidation bases, are generally colorless or weakly colored compounds which may give rise to colored compounds and dyes when combined with oxidizing products via oxidative condensation.

The shades obtained with these oxidation bases may be varied by combining them with couplers or coloration modifiers. Such coloration modifiers may, for example, be chosen from aromatic meta-diamines, aromatic meta-aminophenols, aromatic meta-diphenols and certain heterocyclic compounds. The variety of oxidation bases and couplers may allow a wide range of colors to be obtained.

The so-called "permanent" coloration obtained from using these oxidation dyes should have at least one of the following desirable characteristics. The coloration should have no toxicological drawbacks, the shades obtained should have the desired intensity, and the coloration should have good resistance to external agents to which the fibres may be subjected such as light, bad weather, washing, permanent-waving, perspiration and rubbing. The dyes should allow coverage of grey hair and should be as unselective as possible, that is, they should allow only the smallest possible differences in coloration along the same keratinous fibre which may be differently sensitized (i.e. damaged) between its tip and its root.

Also known in the art are dye compositions containing 2-substituted 5-aminoalkylphenol derivatives for use as couplers. These may be in combination with one or more oxidation bases chosen from, for example, certain para-phenylenediamines, para-aminophenol, para-methylaminophenol, ortho-aminophenol and certain heterocyclic oxidation bases such as 2,5-diaminopyridine and tetraaminopyrimidine. Such dye compositions have been proposed, for example, in patent application JP-2 521 636, the disclosure of which is incorporated herein by reference. However, the colorations obtained using these compositions may not always be sufficiently strong, chromatic and/or resistant to various external agents to which the fibres may be subjected.

The inventors have now discovered that by combining (i) at least one heterocyclic oxidation base chosen from pyrazoles, certain pyrimidines, pyrazolopyrimidines and the acid addition salts thereof and (ii) at least one coupler chosen from 2-substituted 5-aminoalkylphenol derivatives of formula (I) as defined below and the acid addition salts thereof, it may be possible to obtain novel dyes which may result in chromatic, strong, aesthetic colorations in a variety of shades, which may be mainly unselective and which may show satisfactory resistance to one or more external agents to which the fibres may be subjected.

Specifically, one subject of the present invention is compositions for oxidation dyeing of keratin fibres comprising:
(a) at least one heterocyclic oxidation base chosen from:
  i) pyrazoles;
  ii) pyrimidines chosen from diaminopyrimidines, mono- and dihydroxylated diaminopyrimidines, triaminopyrimidines and monohydroxylated triaminopyrimidines;
  iii) pyrazolopyrimidines; and
  iv) the acid addition salts of any of the foregoing; and
(b) at least one coupler chosen from 2-substituted 5-aminoalkylphenol derivatives of formula (I) and the acid addition salts thereof:

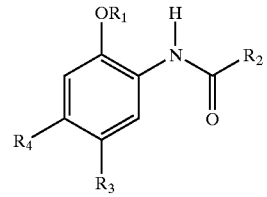

wherein:
$R_1$ is chosen from hydrogen atoms and $C_2$–$C_5$ acyl groups, optionally substituted;
$R_2$ is chosen from hydrogen atoms, $C_1$–$C_4$ alkyl groups, optionally substituted, $C_1$–$C_4$ alkoxy groups, optionally substituted, and amino groups, optionally substituted;
$R_3$ is chosen from hydrogen atoms, halogen atoms, $C_1$–$C_4$ alkoxy groups and $C_1$–$C_4$ monohydroxyalkoxy groups; and
$R_4$ is chosen from $C_1$–$C_4$ alkyl groups, in a medium suitable for dyeing. For example, the keratin fibres may be human keratin fibres, such as hair.

By virtue of the present invention, it may be possible to obtain chromatic, strong, aesthetic colorations in a variety of shades which may show low selectivity and may show excellent properties of withstanding not only at least one atmospheric agent (such as light and bad weather) but may also withstand perspiration and/or various treatments to which the hair may be subjected.

Another subject of the present invention is processes for oxidation dyeing of keratin fibres using the inventive compositions.

According to the present invention, pyrazoles can be chosen from those described in patents DE 3,843,892, DE 4,133,957 and patent applications WO 94/08969, WO 94/08970, FR-A-2,733,749 and DE 195 43 988, the disclosures of which are incorporated herein by reference, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-1-(β-hydroxyethyl) pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3- hydroxymethyl-1-methylpyrazole, 4,5-diamino-3-hydroxyrnethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole and the acid addition salts of any of the foregoing.

Pyrimidines which can be used as the at least one heterocyclic oxidation base in accordance with the present invention comprise 4-hydroxy-2,5,6-triaminopyrimidine, 2-hydroxy-4,5,6-triaminopyrimidine, 6-hydroxy-2,4,5-triaminopyrimidine, 2,4-dihydroxy-5,6-diaminopyrimidine, 2,5,6-triaminopyrimidine and the acid addition salts of any of the foregoing. These compounds are described, for example, in German patent DE 2 359 399 or Japanese patents JP 88-169 571 and JP 91-10659 or in patent application WO 96/15765, the disclosures of which are incorporated herein by reference.

Non-limiting examples of pyrazolopyrimidines which can be used as the at least one heterocyclic oxidation base include those which are mentioned in patent application FR-A-2 750 048, the disclosure of which is incorporated herein by reference, such as, pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-y)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, the acid addition salts of any of the foregoing and the tautomeric forms of any of the foregoing when a tautomeric equilibrium exists.

Suitable 2-substituted 5-aminoalkylphenol derivatives of formula (I) according to the present invention, the synthetic intermediates thereof and processes for preparing them are described in patent application JP-2 521 636, the disclosure of which is incorporated herein by reference.

As previously mentioned, said $R_2$ and said $R_4$ of the formula (I) may be chosen from $C_1$–$C_4$ alkyl groups. Non-limiting examples of said $C_1$–$C_4$ alkyl groups include methyl groups, ethyl groups, n-propyl groups, isopropyl groups, n-butyl groups, sec-butyl groups and tert-butyl groups.

Further, said $R_2$ and said $R_3$ of formula (I) may be chosen from optionally substituted $C_1$–$C_4$ alkoxy groups. Non-limiting examples of $C_1$–$C_4$ alkoxy groups include methoxy groups, ethoxy groups, n-propoxy groups, isopropoxy groups, n-butoxy groups, sec-butoxy groups and tert-butoxy groups.

Said $R_1$ of formula (I) may be chosen from optionally substituted $C_2$–$C_5$ acyl groups. Non-limiting examples of $C_2$–$C_5$ acyl groups include acetyl groups, propanoyl groups, 2,2-dimethylpropanoyl groups, 3-methylpropanoyl groups, butanoyl groups, 2-methylbutanoyl groups and pentanoyl groups.

According to the present invention, said $R_3$ may be chosen from halogen atoms. Non-limiting examples of halogen atoms include fluorine atoms, chlorine atoms, bromine atoms and iodine atoms.

In one embodiment, said $R_1$ is chosen from hydrogen atoms, acetyl groups and propanoyl groups, said $R_2$ is chosen from methyl groups, ethyl groups, methoxy groups and amino groups, said $R_3$ is chosen from hydrogen atoms and methoxy groups, and said $R_4$ is chosen from methyl groups and ethyl groups. alkoxy groups and $C_2$–$C_5$ acyl groups comprised in formula (I) include halogen atoms (such as fluorine atoms, chlorine atoms, bromine atoms and iodine atoms), $C_1$–$C_4$ alkoxy groups (such as methoxy groups, ethoxy groups, n-propoxy groups, isopropoxy groups, n-butoxy groups, sec-butoxy groups and tert-butoxy groups), $C_2$–$C_5$ alkanoyloxy groups (such as acetoxy groups, propanoyloxy groups, 2,2-dimethylpropanoyloxy groups, 3-methylpropanoyloxy groups, butanoyloxy groups, 2-methylbutanoyloxy groups and pentanoyloxy groups), hydroxyl groups, amino group, amino groups protected with at least one protecting group, carboxyl groups and $C_2$–$C_5$ alkoxycarbonyl groups (such as methoxycarbonyl groups, ethoxycarbonyl groups, n-propoxycarbonyl groups, isopropoxycarbonyl groups, n-butoxycarbonyl groups, sec-butoxycarbonyl groups and tert-butoxycarbonyl groups). In one embodiment substituents are chosen from methoxy groups and hydroxyl groups.

For example, said at least one protecting group can be chosen from tert-butoxycarbonyl groups and benzyloxycarbonyl groups.

As previously mentioned, said $R_2$ can be chosen from substituted amino groups. Non-limiting examples of substituents which may be used according to the present invention include $C_1$–$C_4$ alkyl groups optionally substituted with at least one hydroxyl group. In one embodiment, the substituents are chosen from hydroxyethyl groups.

In another embodiment, said 2-substituted 5-aminoalkylphenol derivatives of formula (I) are chosen from:

N-(2-hydroxy-4-methylphenyl)formamide,
N-(2-hydroxy-4-methylphenyl) methylcarbamate,
N-(2-hydroxy-4-methylphenyl)urea,
N-(2-hydroxy-4-methylphenyl)-N'-(2-hydroxyethyl) urea,
N-(2-hydroxy-4-methylphenyl)acetamide,
N-(2-hydroxy-4-methylphenyl)chloroacetamide,
N-(2-hydroxy-4-methylphenyl)acetoxyacetamide,
N-(2-hydroxy-4-methylphenyl)hydroxyacetamide,
N-(2-hydroxy-4-methylphenyl)methoxyacetamide,
N-(2-hydroxy-4-methylphenyl)aminoacetamide,
N-(2-hydroxy-4-methylphenyl)propionamide,
N-(2-hydroxy-4-methylphenyl)-2-hydroxypropionamide,
N-(2-hydroxy-4-methylphenyl)-3-aminopropionamide,
N-(2-hydroxy-4-methylphenyl)butanamide,
N-(2-hydroxy-4-methylphenyl)-4-chlorobutanamide,
N-(2-hydroxy-4-methylphenyl)succinamide,
N-(2-hydroxy-4-isopropylphenyl)acetamide,
2'-acetamido-5'-methylphenyl acetate,
2'-propionamido-5'-methylphenyl propionate,
N-(2-hydroxy-5-methoxy-4-methylphenyl)acetamide, and
the acid addition salts of any of the foregoing.

The at least one heterocyclic oxidation base may be present in an amount generally ranging from about 0.0005% to about 12% by weight relative to the total weight of the composition, such as from about 0.005% to about 6% by weight.

The at least one coupler chosen from 2-substituted 5-aminoalkylphenol derivatives of formula (I) and the acid addition salts thereof may be present in an amount generally ranging from about 0.0005% to about 12% by weight relative to the total weight of the composition, such as from about 0.005% to about 6% by weight.

According to the present invention, the compositions can optionally further comprise at least one additional oxidation base different from the at least one heterocyclic oxidation base as defined above, can optionally further comprise at least one additional coupler different from the at least one coupler of formula (I) and can optionally further comprise at least one direct dye.

Non-limiting examples of the at least one additional coupler include meta-phenylenediamines, meta-aminophenols, meta-diphenols, heterocyclic couplers and the acid addition salts of any of the foregoing. For example, heterocyclic couplers which may used according to the present invention are indole derivatives, indoline derivatives, benzimidazole derivatives, benzomorpholine derivatives, sesamol derivatives, pyridine derivatives, pyrimidine derivatives, pyrazole derivatives and the acid addition salts of any of the foregoing.

In one embodiment, the at least one additional coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 2-methyl-1-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one and the acid addition salts of any of the foregoing.

In general, the acid addition salts which can be used according to the present invention may be chosen from hydrochlorides, hydrobromides, sulphates, tartrates, lactates and acetates.

As previously mentioned, the inventive compositions comprise a medium suitable for dyeing. The medium suitable for dyeing, which can also be considered as the support for the dyeing composition, can be chosen from water and a mixture of water and at least one organic solvent if the compounds are not sufficiently soluble in water alone. The at least one organic solvent may be chosen from $C_1$–$C_4$ alkanols, glycerol, glycols, glycol ethers and aromatic alcohols. Non-limiting examples of $C_1$–$C_4$ alkanols are ethanol and isopropanol, and examples of glycols and glycol ethers are 2-butoxyethanol, propylene glycol, propylene glycol monomethyl ether, diethylene glycol monoethyl ether and diethylene glycol monomethyl ether. Representative aromatic alcohols are benzyl alcohol and phenoxy ethanol.

The at least one organic solvent, if present, generally ranges from 1% to about 40% by weight relative to the total weight of the composition, such as from about 5% to about 30%.

According to the present invention, the pH of the inventive composition generally ranges from about 3 to about 12, such as from about 5 to about 12. The pH may be adjusted to a desired value using acidifying or basifying agents suitable for use in compositions for dyeing of keratin fibres.

Acidifying agents which may be used according to the present invention can be chosen from inorganic acids and organic acids. For example, the acidifying agents can be chosen from hydrochloric acid, orthophosphoric acid, sulphuric acid, carboxylic acids such as acetic acid, tartaric acid, citric acid and lactic acid, and sulphonic acids.

Basifying agents which may be used according to the present invention can be chosen from aqueous ammonia, alkaline carbonates, alkanolamines such as mono-ethanolamines, di-ethanolamines and tri-ethanolamines, 2-methyl-2-amino-1-propanol and derivatives thereof, sodium hydroxide, potassium hydroxide and compounds of formula (II):

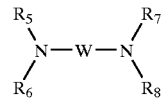

(II)

wherein:
W is chosen from propylene groups, optionally substituted with at least one group chosen from hydroxyl groups and $C_1$–$C_4$ alkyl groups; and
$R_5$, $R_6$, $R_7$ and $R_8$, which may be identical or different, are each chosen from hydrogen atoms, $C_1$–$C_4$ alkyl groups and $C_1$–$C_4$ hydroxyalkyl groups.

According to the present invention, the compositions can further comprise at least one suitable additive conventionally used in compositions for dyeing hair chosen from anionic surfactants, cationic surfactants, nonionic surfactants, amphoteric surfactants, zwitterionic surfactants, anionic polymers, cationic polymers, nonionic polymers, amphoteric polymers, zwitterionic polymers, inorganic thickeners, organic thickeners such as, for example, non-ionic guar gums, antioxidants, penetration agents, sequestering agents, fragrances, buffers, dispersing agents, optionally modified conditioners such as, for example, volatile and non-volatile silicones, film-forming agents, ceramides, preserving agents and opacifiers.

Needless to say, a person skilled in the art will take care to select the at least one suitable additive such that the advantageous properties intrinsically associated with the composition in accordance with the invention are not, or are not substantially, adversely affected by the addition(s) envisaged.

In the present invention, the inventive compositions can be in the form of liquids, creams, mousses or gels, which may optionally be pressurized, or in any other form which is suitable for dyeing keratin fibres, such as human hair.

As previously mentioned, another subject of the present invention is processes for dyeing keratin fibres comprising using at least one inventive composition as defined above. According to one inventive process, at least one dye composition as defined above is applied to the said keratin fibres for a sufficient time to develop a desired color. The desired color can be developed at acidic, neutral or alkaline pH using at least one oxidizing agent. Further, the at least one oxidizing agent can optionally be added to said at least one dye composition, prior to use, such as immediately prior to use, and can optionally be comprised in at least one oxidizing composition. The oxidizing composition can optionally be applied to the keratin fibres simultaneously with the least one dye composition and can optionally be applied to the keratin fibres sequentially with, and separately from, the least one dye composition.

In one embodiment, the at least one dye composition is mixed, at the time of use, with at least one oxidizing composition comprising, in a medium suitable for dyeing, at least one oxidizing agent which is present in an amount sufficient to develop a desired coloration. The resulting mixture is then applied to the keratin fibres and is left on the keratin fibres, for example, for about 3 to about 50 minutes, such as from about 5 to about 30 minutes, after which the fibres may be rinsed, washed with shampoo, rinsed again and dried.

According to the present invention, the at least one oxidizing agent may be chosen from oxidizing agents conventionally used for the oxidation dyeing of keratin fibres. Non-limiting examples of such oxidizing agents include hydrogen peroxide, urea peroxide, alkali metal bromates, persalts such as perborates and persulphates, peracids and enzymes such as peroxidases, 2-electron oxidoreductases (such as uricases) and 4-electron oxygenases (such as laccases). In one embodiment, the at least one oxidizing agent is chosen from hydrogen peroxide.

The pH of the composition resulting from mixing the at least one oxidizing composition with the at least one dye composition generally ranges from about 3 to about 12, such as from about 5 to about 11. The pH of the resultant composition may be adjusted to a desired value using acidifying or basifying agents suitable for use in dyeing of keratin fibres, such as those defined above.

According to the present invention, the at least one oxidizing composition may further comprise at least one suitable additive conventionally used in dye compositions, such as those defined above.

The inventive compositions which are applied to the keratin fibres can be in the form of liquids, creams, mousses or gels, which may optionally be pressurized, or in any other form which is suitable for at least one keratinous fibre, such as human hair.

Another subject of the present invention is a multi-compartment dyeing device or kit comprising (a) a first compartment comprising a first composition and (b) a second compartment comprising a second composition, wherein said first composition comprises at least one dye composition comprising:
(A) at least one heterocyclic oxidation base chosen from:
   i) pyrazoles;
   ii) pyrimidines chosen from diaminopyrimidines, mono- and dihydroxylated diaminopyrimidines, triaminopyrimidines and monohydroxylated triaminopyrimidines;
   iii) pyrazolopyrimidines; and
   iv) the acid addition salts of any of the foregoing; and
(B) at least one coupler chosen from 2-substituted 5-aminoalkylphenol derivatives of formula (I) and the acid addition salts thereof:

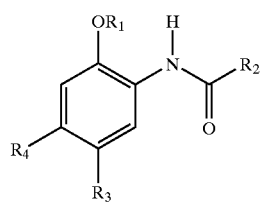

(I)

wherein:
R$_1$ is chosen from hydrogen atoms and C$_2$–C$_5$ acyl groups, optionally substituted;
R$_2$ is chosen from hydrogen atoms, C$_1$–C$_4$ alkyl groups, optionally substituted, C$_1$–C$_4$ alkoxy groups, optionally substituted, and amino groups, optionally substituted;
R$_3$ is chosen from hydrogen atoms, halogen atoms, C$_1$–C$_4$ alkoxy groups and C$_1$–C$_4$ monohydroxyalkoxy groups; and
R$_4$ is chosen from C$_1$–C$_4$ alkyl groups; and
wherein said second composition comprises at least one oxidizing composition as defined above.

These devices may be equipped with a means for applying the desired mixture to the hair, such as the devices described in patent FR-2 586 913 in the name of L'Oreal, the disclosure of which is incorporated herein by reference.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result. The percentages are given on a weight basis.

EXAMPLES

Examples 1 to 3 of Dyeing in Alkaline Medium

The dye compositions below, in accordance with the invention, were prepared:

| EXAMPLE | 1 | 2 | 3 |
|---|---|---|---|
| 4,5-Diamino-1-ethyl-3-methylpyrazole dihydrochloride (heterocyclic oxidation base) | 3 × 10$^{-3}$ mol | — | — |
| 2,4,5-Triamino-6-hydroxypyrimidine sulphate (heterocyclic oxidation base) | — | 3 × 10$^{-3}$ mol | — |
| Pyrazolo[1,5-a]pyrimidine-3,7-diamine dihydrochloride (heterocyclic oxidation base) | — | — | 3 × 10$^{-3}$ mol |
| N-(2-Hydroxy-4-methylphenyl)acetamide (coupler of formula (I) in accordance with the invention) | 3 × 10$^{-3}$ mol | 3 × 10$^{-3}$ mol | 3 × 10$^{-3}$ mol |
| Common dye support | (*) | (*) | (*) |
| Demineralized water qs | 100 g | 100 g | 100 g |

(*) Common dye support:

| | |
|---|---|
| (C$_8$–C$_{10}$) Alkylpolyglucoside as an aqueous 60% solution, sold under the name Oramix CG 110 ® by the company SEPPIC | 5.4 g |
| Ethanol | 18.0 g |
| Benzyl alcohol | 1.8 g |

-continued

| EXAMPLE | 1 | 2 | 3 |
|---|---|---|---|
| Polyethylene glycol 400 | | | 2.7 g |
| Pentasodium salt of diethylenetriamine pentaacetic acid, as an aqueous 40% solution, sold under the name Dissoluine D-40 ® by the company Akzo | | | 1.08 g |
| Sodium metabisulphite | | | 0.205 g |
| Aqueous ammonia containing 20.5% $NH_3$ | | | 10.0 g |

At the time of use, each of the dye compositions described above was mixed weight for weight with a 20-volumes hydrogen peroxide solution (6% by weight).

Each of the mixtures thus prepared was applied for 30 minutes to locks of natural grey 90% white hairs. The locks were then rinsed, washed with a standard shampoo, rinsed again and then dried.

The hair was dyed in a shade given in the table below:

| EXAMPLE | SHADE OBTAINED |
|---|---|
| 1 | Mid violet |
| 2 | Golden light blonde |
| 3 | Strong purple |

Comparative Dyeing Examples 4 to 6

The dye compositions below were prepared:

| EXAMPLE | 4 (**) | 5 | 6 |
|---|---|---|---|
| para-Phenylenediamine (oxidation base not forming part of the invention) | $3 \times 10^{-3}$ mol | — | — |
| 2,4,5-Triamino-6-hydroxypyrimidine sulphate (heterocyclic oxidation base) | — | $3 \times 10^{-3}$ mol | — |
| Pyrazolo[1,5-a]pyrimidine-3,7-diamine dihydrochloride (heterocyclic oxidation base) | — | — | $3 \times 10^{-3}$ mol |
| N(2-Hydroxy-4-methylphenyl)acetamide (coupler of formula (I) in accordance with the invention) | $3 \times 10^{-3}$ mol | $3 \times 10^{-3}$ mol | $3 \times 10^{-3}$ mol |
| Common dye support | (*) | (*) | (*) |
| Demineralized water qs | 100 g | 100 g | 100 g |

(**): Composition not forming part of the invention.
(*) Common dye support:
This is identical to the one used in Examples 1 to 3.

Each of the above dye compositions was then applied to locks of natural grey hair containing 90% white hairs, under the conditions described above for Examples 1 to 3.

The colour of the locks thus dyed was then evaluated in the L*.a*.b* system, using a Minolta CM2002® spectrophotometer in order to calculate the chromaticity (luminosity) of the colorations obtained.

In the L*a*b* system, the three parameters respectively denote the intensity (L*), the shade (a*) and the saturation (b*).

According to this system, the higher the value of L*, the lighter or less intense the colour. Conversely, the lower the value of L*, the darker or more intense the colour.

a* and b* indicate two colour axes, a* indicating the green/red colour axis and b* indicating the blue/yellow colour axis. Values close to zero for a* and b* correspond to grey shades.

The chromaticity of the coloration (C) can be calculated by applying the following equation:

$$C = \sqrt{a^{*2} + b^{*2}}$$

In this equation, C represents the Chromaticity of the lock dyed, $a^{*2}$ and $b^{*2}$ respectively represent the shade and saturation of the dyed lock raised to the power of two.

The larger the value of C, the greater the Chromaticity (or luminosity) of the coloration.

The results obtained are given in the table below:

| EXAMPLE | a* | b* | C |
|---|---|---|---|
| 4(**) | 0.64 | −7.94 | 8.0 |
| 5 | 2.77 | 12 | 12.3 |
| 6 | 11.2 | −5.69 | 12.6 |

(**): Example not forming part of the invention

These results show that the dye compositions of Examples 5 and 6 in accordance with the invention, i.e. the composition containing the combination of a heterocyclic oxidation base in accordance with the invention and N-(2-hydroxy-4-methylphenyl)acetamide as coupler, lead to colorations which are markedly more chromatic than that obtained with the composition of Example 4 not forming part of the invention, since in this composition the heterocyclic oxidation base has been replaced with an oxidation base not forming part of the invention, namely para-phenylenediamine.

Comparative Examples 7 and 8

The dye compositions below were prepared:

| EXAMPLE | 7 | 8 (**) |
|---|---|---|
| 4,5-Diamino-1-ethyl-3-methylpyrazole dihydrochloride (heterocyclic oxidation base) | $3 \times 10^{-3}$ mol | — |
| para-Phenylenediamine (oxidation base not forming part of the invention) | — | $3 \times 10^{-3}$ mol |
| N-(2-Hydroxy-4-methylphenyl)-acetamide (coupler of formula (I) in accordance with the invention) | $3 \times 10^{-3}$ mol | $3 \times 10^{-3}$ mol |
| Common dye support | (*) | (*) |
| Demineralized water qs | 100 g | 100 g |

(**): Composition not forming part of the invention.
(*) Common dye support:
This is identical to the one used in Examples 1 to 3.

Each of the above dye compositions was then applied to locks of permed grey hair containing 90% white hairs, under the conditions described above for Examples 1 to 3.

The colour of the locks thus dyed was then evaluated in the L*.a*.b* system, using a Minolta CM2002® spectrophotometer in order to calculate the chromaticity (luminosity) of the colorations obtained, in the same way as for Examples 4 to 6 above.

The results obtained are given in the table below:

| EXAMPLE | a* | b* | C |
|---|---|---|---|
| 7 | 5.99 | −16.22 | 17.3 |
| 8(**) | 0.81 | −11.58 | 11.6 |

(**): Example not forming part of the invention

These results show that the dye composition of Example 7 in accordance with the invention, i.e. the composition containing the combination of a heterocyclic oxidation base in accordance with the invention and N-(2-hydroxy-4-methylphenyl)-acetamide as coupler, leads to colorations which are markedly more chromatic than that obtained with the composition of Example 8 not forming part of the invention, since in this composition the heterocyclic oxidation base has been replaced with an oxidation base not forming part of the invention, namely para-phenylenediamine.

What we claim is:

1. A composition for oxidation dyeing of keratin fibres comprising:
   (a) at least one heterocyclic oxidation base chosen from:
      i) pyrazoles;
      ii) pyrimidines chosen from diaminopyrimidines, mono- and dihydroxylated diaminopyrimidines, triaminopyrimidines and monohydroxylated triaminopyrimidines;
      iii) pyrazolopyrimidines; and
      iv) the acid addition salts thereof; and
   (b) at least one coupler chosen from 2-substituted 5-aminoalkylphenol derivatives of formula (I) and the acid addition salts thereof:

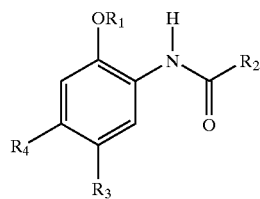

(I)

wherein:
   $R_1$ is chosen from hydrogen atoms and $C_2$–$C_5$ acyl groups, optionally substituted;
   $R_2$ is chosen from hydrogen atoms, $C_1$–$C_4$ alkyl groups, optionally substituted, $C_1$–$C_4$ alkoxy groups, optionally substituted, and amino groups, optionally substituted;
   $R_3$ is chosen from hydrogen atoms, halogen atoms, $C_1$–$C_4$ alkoxy groups and $C_1$–$C_4$ monohydroxyalkoxy groups; and
   $R_4$ is chosen from $C_1$–$C_4$ alkyl groups, in a medium suitable for dyeing.

2. A composition according to claim 1, wherein said keratin fibres are human keratin fibres.

3. A composition according to claim 2, wherein said human keratin fibres are hair.

4. A composition according to claim 1, wherein said pyrazoles are chosen from 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-1-(β-hydroxyethyl)pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole and the acid addition salts of any of the foregoing.

5. A composition according to claim 1, wherein said pyrimidines are chosen from 4-hydroxy-2,5,6-triaminopyrimidine, 2-hydroxy-4,5,6-triaminopyrimidine, 6-hydroxy-2,4,5-triaminopyrimidine, 2,4-dihydroxy-5,6-diaminopyrimidine, 2,5,6-triaminopyrimidine and the acid addition salts of any of the foregoing.

6. A composition according to claim 1, wherein said pyrazolopyrimidines are chosen from pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine and the acid addition salts of any of the foregoing and the tautomeric forms of any of the foregoing when a tautomeric equilibrium exists.

7. A composition according to claim 1, wherein said $C_1$–$C_4$ alkyl groups of formula (I) are chosen from methyl groups, ethyl groups, n-propyl groups, isopropyl groups, n-butyl groups, sec-butyl groups and tert-butyl groups.

8. A composition according to claim 1, wherein said $C_1$–$C_4$ alkoxy groups of formula (I) are chosen from methoxy groups, ethoxy groups, n-propoxy groups, isopropoxy groups, n-butoxy groups, sec-butoxy groups and tert-butoxy groups.

9. A composition according to claim 1, wherein said $C_2$–$C_5$ acyl groups of formula (I) are chosen from acetyl groups, propanoyl groups, 2,2-dimethylpropanoyl groups, 3-methylpropanoyl groups, butanoyl groups, 2-methylbutanoyl groups and pentanoyl groups.

10. A composition according to claim 1, wherein said halogen atoms are chosen from fluorine atoms, chlorine atoms, bromine atoms and iodine atoms.

11. A composition according to claim 1, wherein said $R_1$ is chosen from hydrogen atoms, acetyl groups and propanoyl groups, said $R_2$ is chosen from methyl groups, ethyl groups, methoxy groups and amino groups, said $R_3$ is chosen from hydrogen atoms and methoxy groups, and said $R_4$ is chosen from methyl groups and ethyl groups.

12. A composition according to claim 1, wherein said substituents on said optionally substituted groups of formula (I) are chosen from halogen atoms, $C_1$–$C_4$ alkoxy groups, $C_2$–$C_5$ alkanoyloxy groups, hydroxyl groups, amino group, amino groups protected with at least one protecting group, carboxyl groups and $C_2$–$C_5$ alkoxycarbonyl groups.

13. A composition according to claim 12, wherein said halogen atoms are chosen from fluorine atoms, chlorine atoms, bromine atoms and iodine atoms.

14. A composition according to claim 12, wherein said $C_1$–$C_4$ alkoxy groups are chosen from methoxy groups, ethoxy groups, n-propoxy groups, isopropoxy groups, n-butoxy groups, sec-butoxy groups and tert-butoxy groups.

15. A composition according to claim 12, wherein said $C_2$–$C_5$ alkanoyloxy groups are chosen from acetoxy groups, propanoyloxy groups, 2,2-dimethylpropanoyloxy groups, 3-methylpropanoyloxy groups, butanoyloxy groups, 2-methylbutanoyloxy groups and pentanoyloxy groups.

16. A composition according to claim 12, wherein said $C_2$–$C_5$ alkoxycarbonyl groups are chosen from methoxycarbonyl groups, ethoxycarbonyl groups, n-propoxycarbonyl groups, isopropoxycarbonyl groups, n-butoxycarbonyl groups, sec-butoxycarbonyl groups and tert-butoxycarbonyl groups.

17. A composition according to claim 12, wherein said substituents are chosen from methoxy groups and hydroxyl groups.

18. A composition according to claim 12, wherein said at least one protecting group is chosen from tert-butoxycarbonyl groups and benzyloxycarbonyl groups.

19. A composition according to claim 1, wherein said $R_2$ is chosen from amino groups substituted with at least one group chosen from $C_1$–$C_4$ alkyl groups optionally substituted with at least one hydroxyl group.

20. A composition according to claim 19, wherein said at least one group is chosen from hydroxyethyl groups.

21. A composition according to claim 1, wherein said 2-substituted 5-aminoalkylphenol derivatives of formula (I) are chosen from:

N-(2-hydroxy-4-methylphenyl)formamide,
N-(2-hydroxy-4-methylphenyl) methylcarbamate,
N-(2-hydroxy-4-methylphenyl)urea,
N-(2-hydroxy-4-methylphenyl)-N'-(2-hydroxyethyl)urea,
N-(2-hydroxy-4-methylphenyl)acetamide,
N-(2-hydroxy-4-methylphenyl)chloroacetamide,
N-(2-hydroxy-4-methylphenyl)acetoxyacetamide,
N-(2-hydroxy-4-methylphenyl)hydroxyacetamide,
N-(2-hydroxy-4-methylphenyl)methoxyacetamide,
N-(2-hydroxy-4-methylphenyl)aminoacetamide,
N-(2-hydroxy-4-methylphenyl)propionamide,
N-(2-hydroxy-4-methylphenyl)-2-hydroxypropionamide,
N-(2-hydroxy-4-methylphenyl)-3-aminopropionamide,
N-(2-hydroxy-4-methylphenyl)butanamide,
N-(2-hydroxy-4-methylphenyl)-4-chlorobutanamide,
N-(2-hydroxy-4-methylphenyl)succinamide,
N-(2-hydroxy-4-isopropylphenyl)acetamide,
2'-acetamido-5'-methylphenyl acetate,
2'-propionamido-5'-methylphenyl propionate,
N-(2-hydroxy-5-methoxy-4-methylphenyl)acetamide, and
the acid addition salts of any of the foregoing.

22. A composition according to claim 1, wherein said at least one heterocyclic oxidation base is present in an amount ranging from about 0.0005% to about 12% by weight relative to the total weight of said composition.

23. A composition according to claim 22, wherein said at least one heterocyclic oxidation base is present in an amount ranging from about 0.005% to about 6% by weight relative to the total weight of said composition.

24. A composition according to claim 1, wherein said at least one coupler is present in an amount ranging from about 0.0005% to about 12% by weight relative to the total weight of said composition.

25. A composition according to claim 24, wherein said at least one coupler is present in an amount ranging from about 0.005% to about 6% by weight relative to the total weight of said composition.

26. A composition according to claim 1, further comprising at least one additional oxidation base different from said at least one heterocyclic oxidation base as defined in claim 1.

27. A composition according to claim 1, further comprising at least one additional coupler different from said at least one coupler of formula (I).

28. A composition according to claim 1, further comprising at least one direct dye.

29. A composition according to claim 27, wherein said at least one additional coupler is chosen from meta-phenylenediamines, meta-aminophenols, meta-diphenols, heterocyclic couplers and the acid addition salts of any of the foregoing.

30. A composition according to claim 29, wherein said heterocyclic couplers are chosen from indole derivatives, indoline derivatives, benzimidazole derivatives, benzomorpholine derivatives, sesamol derivatives, pyridine derivatives, pyrimidine derivatives, pyrazole derivatives and the acid addition salts of any of the foregoing.

31. A composition according to claim 27, wherein said at least one additional coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diamrinophenoxy)propane, sesamol, 1-amino-2-methoxy-4,5-methylenedioxybenzene, α-naphthol, 2-methyl-1-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one and the acid addition salts of any of the foregoing.

32. A composition according to claim 1, wherein said acid addition salts are chosen from hydrochlorides, hydrobromides, sulphates, tartrates, lactates and acetates.

33. A composition according to claim 1, wherein said medium suitable for dyeing is chosen from water and a mixture of water and at least one organic solvent.

34. A composition according to claim 33, wherein said at least one organic solvent is chosen from $C_1$–$C_4$ lower alkanols, glycerol, glycols, glycol ethers and aromatic alcohols.

35. A composition according to claim 34, wherein said $C_1$–$C_4$ lower alkanols are chosen from ethanol and isopropanol.

36. A composition according to claim 34, wherein said glycols and glycol ethers are chosen from 2-butoxyethanol, propylene glycol, propylene glycol monomethyl ether, diethylene glycol mohoethyl ether and diethylene glycol monomethyl ether.

37. A composition according to claim 34, wherein said aromatic alcohols are chosen from benzyl alcohol and phenoxy alcohol.

38. A composition according to claim 1, wherein said medium suitable for dyeing is present in a proportion ranging from about 1% to about 40% by weight relative to the total weight of said composition.

39. A composition according to claim 38, wherein said medium suitable for dyeing is present in a proportion ranging from about 5% to about 30% by weight relative to the total weight of said composition.

40. A composition according to claim 1 having a pH ranging from about 3 to about 12.

41. A composition according to claim 40, wherein said pH ranges from about 5 to about 12.

42. A composition according to claim 1, further comprising at least one suitable additive chosen from anionic surfactants, cationic surfactants, nonionic surfactants, amphoteric surfactant, zwitterionic surfactant, anionic polymers, cationic polymers, nonionic polymers, amphoteric polymers, zwitterionic polymers, inorganic thickening agents, organic thickening agents, antioxidants, penetrating agents, sequestering agents, fragrances, buffers, dispersing agents, optionally modified conditioners, film-forming agents, ceramides, preservatives and opacifiers.

43. A composition according to claim 42, wherein said organic thickening agents are chosen from nonionic guar gums.

44. A composition according to claim 42, wherein said optionally modified conditioners are chosen from volatile and non-volatile silicones.

45. A composition according to claim 1, in the form of a liquid, a cream, a gel or any other suitable form which is suitable for dyeing keratin fibres.

46. A process for dyeing keratinous fibers comprising applying to said keratinous fibers for a sufficient time to develop a desired color at least one dye composition comprising:
(a) at least one heterocyclic oxidation base chosen from:
  i) pyrazoles;
  ii) pyrimidines chosen from diaminopyrimidines, mono- and dihydroxylated diaminopyrimidines, triaminopyrimidines and monohydroxylated triaminopyrimidines;
  iii) pyrazolopyrimidines; and
  iv) the acid addition salts thereof; and
(b) at least one coupler chosen from 2-substituted 5-aminoalkylphenol derivatives of formula (I) and the acid addition salts thereof:

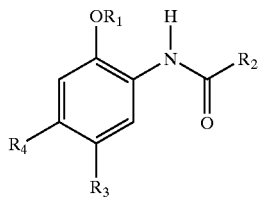

(I)

wherein:
$R_1$ is chosen from hydrogen atoms and $C_2$–$C_5$ acyl groups, optionally substituted;
$R_2$ is chosen from hydrogen atoms, $C_1$–$C_4$ alkyl groups, optionally substituted, $C_1$–$C_4$ alkoxy groups, optionally substituted, and amino groups, optionally substituted;
$R_3$ is chosen from hydrogen atoms, halogen atoms, $C_1$–$C_4$ alkoxy groups and $C_1$–$C_4$ monohydroxyalkoxy groups; and
$R_4$ is chosen from $C_1$–$C_4$ alkyl groups, in a medium suitable for dyeing.

47. A process according to claim 46, wherein said desired color is developed at acidic, neutral or alkaline pH using at least one oxidizing agent.

48. A process according to claim 46, wherein said at least one oxidizing agent is added to said at least one dyeing composition prior to said applying.

49. A process according to claim 46, wherein said at least one oxidizing agent is comprised in at least one oxidizing composition.

50. A process according to claim 49, wherein said at least one oxidizing composition is applied to said keratinous fibres simultaneously with said at least one dyeing composition.

51. A process according to claim 49, wherein said at least one oxidizing composition is applied to said keratinous fibres sequentially with said at least one dyeing composition.

52. A process according to claim 46, wherein said keratinous fibres are human keratin fibres.

53. A process according to claim 52, wherein said human keratin fibres are hair.

54. A process according to claim 46, wherein said sufficient time to develop a desired color ranges from about 3 minutes to about 50 minutes.

55. A process according to claim 54, wherein said sufficient time to develop a desired color ranges from about 5 minutes to about 30 minutes.

56. A process according to claim 46, further comprising rinsing said keratinous fibres.

57. A process according to claim 56, further comprising washing said keratinous fibres with shampoo.

58. A process according to claim 57, further comprising rinsing said keratinous fibres after said washing.

59. A process according to claim 46, wherein said at least one oxidizing agent is chosen from hydrogen peroxide, urea peroxide, alkali metal bromates, persalts and enzymes.

60. A process according to claim 59, wherein said persalts are chosen from perborates and persulphates.

61. A process according to claim 59, wherein said enzymes are chosen from peroxidases, 2-electron oxidoreductases and 4-electron oxygenases.

62. A process according to claim 61, wherein said 2-electron oxidoreductases are chosen from uricases.

63. A process according to claim 61, wherein said 4-electron oxidoreductases are chosen from laccases.

64. A process according to claim 61, wherein said at least one oxidizing agent is chosen from hydrogen peroxide.

65. A multi-compartment dyeing device or kit comprising:
(a) a first compartment comprising a first composition
(b) a second compartment comprising a second composition
wherein said first composition comprises at least one dye composition comprising:
  (A) at least one heterocyclic oxidation base chosen from:
    i) pyrazoles;
    ii) pyrimidines chosen from diaminopyrimidines, mono- and dihydroxylated diaminopyrimidines, triaminopyrimidines and monohydroxylated triaminopyrimidines;
    iii) pyrazolopyrimidines; and
    iv) the acid addition salts thereof; and
  (B) at least one coupler chosen from 2-substituted 5-aminoalkylphenol derivatives of formula (I) and the acid addition salts thereof:

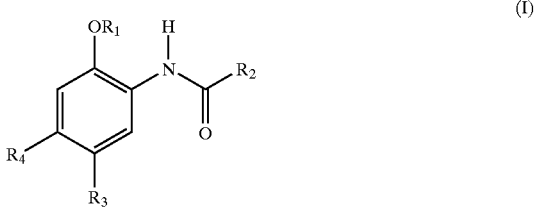

(I)

wherein:
$R_1$ is chosen from hydrogen atoms and $C_2$–$C_5$ acyl groups, optionally substituted;
$R_2$ is chosen from hydrogen atoms, $C_1$–$C_4$ alkyl groups, optionally substituted, $C_1$–$C_4$ alkoxy groups, optionally substituted, and amino groups, optionally substituted;
$R_3$ is chosen from hydrogen atoms, halogen atoms, $C_1$–$C_4$ alkoxy groups and $C_1$–$C_4$ monohydroxyalkoxy groups; and
$R_4$ is chosen from $C_1$–$C_4$ alkyl groups,
in a medium suitable for dyeing; and
wherein said second composition comprises at least one oxidizing composition.

* * * * *

UNITED STATES PATENT AND TRADEMARK OFFICE
CERTIFICATE OF CORRECTION

PATENT NO.     : 6,752,839 B1
DATED          : June 22, 2004
INVENTOR(S)    : Florent Pastore and Alain Lagrange It is certified that error appears in the above-identified patent and that said Letters Patent is hereby corrected as shown below:

Title page,
Item [*] Notice, "Subject to any disclaimer, the term of this patent is extended or adjusted under 35 U.S.C., 154(b) by 142 days." should read -- Subject to any disclaimer, the term of this patent is extended or adjusted under 35 U.S.C. 154(b) by 547 days. --

Column 14,
Line 22, "1,3-bis(2,4-diamrinophenoxy)propane," should read -- 1,3-bis(2,4-diaminophenoxy)propane, --.
Line 44, "mohoethyl" should read -- monoethyl --.

Signed and Sealed this

Twelfth Day of October, 2004

JON W. DUDAS
*Director of the United States Patent and Trademark Office*